United States Patent [19]

Blumenfeld et al.

[11] 4,134,934
[45] Jan. 16, 1979

[54] SOLUTION OF AN UNSATURATED POLYESTER AND A COPOLYMERIZABLE MONOMER

[75] Inventors: Georg Blumenfeld, St. Augustin; Norbert Vollkommer, Troisdorf, both of Germany

[73] Assignee: Dynamit Nobel Aktiengesellschaft, Troisdorf, Germany

[21] Appl. No.: 868,106

[22] Filed: Jan. 9, 1978

Related U.S. Application Data

[60] Division of Ser. No. 640,312, Dec. 12, 1975, which is a continuation of Ser. No. 488,601, Jul. 12, 1974, abandoned.

[30] Foreign Application Priority Data

Jul. 19, 1973 [DE] Fed. Rep. of Germany ....... 2336704

[51] Int. Cl.$^2$ .................... C08L 67/06; C08G 63/68
[52] U.S. Cl. .................... 260/869; 260/861; 260/DIG. 24; 528/299
[58] Field of Search .............. 260/861, 869, 75 H, 260/DIG. 24

[56] References Cited

U.S. PATENT DOCUMENTS

| | | | |
|---|---|---|---|
| 2,621,168 | 12/1952 | Ross et al. | 260/75 H |
| 2,631,168 | 3/1953 | Ross et al. | 260/75 H X |
| 2,967,854 | 1/1961 | Bungs | 260/75 UA |
| 3,826,806 | 7/1974 | Comstock et al. | 260/75 H X |

FOREIGN PATENT DOCUMENTS 1126609 3/1962 Fed. Rep. of Germany.
836530 6/1960 United Kingdom.

*Primary Examiner*—Walter C. Danison
*Attorney, Agent, or Firm*—Sprung, Felfe, Horn, Lynch & Kramer

[57] ABSTRACT

An improvement in an unsaturated polyesters having recurring units of the formula

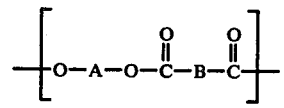

wherein A is the residue of an alcoholic moiety and B is the residue of an acid moiety, which improvement resides in the fact that some of the A residues are chloroxylylene containing residues having the formula

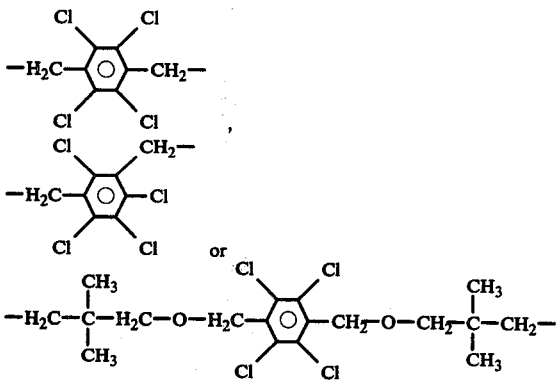

4 Claims, No Drawings

SOLUTION OF AN UNSATURATED POLYESTER AND A COPOLYMERIZABLE MONOMER

This is a division, of application Ser. No. 640,312, filed Dec. 12, 1975, which is a continuation of application Ser. No. 488,601, filed July 12, 1974, now abandoned.

BACKGROUND OF THE INVENTION

1. Field of the Invention

This invention relates to unsaturated polyesters which are derived from an acid component of an unsaturated and, in some cases saturated dicarboxylic acid and an alcohol component, particularly a polyvalent alcohol component. More particularly, this invention is directed to thermally stable unsaturated polyesters and to unsaturated polyesters which can be formed into finished articles possessing high thermal stability. More especially this invention is directed to unsaturated polyesters wherein at least a portion of the compounds which are condensed with the compound containing the acid moiety are certain chloroxylylene containing compounds. This invention is particularly addressed to resinous solutions unsaturated polyesters which possess good shelf life.

2. Discussion of Prior Art

Unsaturated polyesters which are derived, as regards the acid component, from unsaturated and, in some cases, saturated dicarboxylic acids or dicarboxylic acid mixtures, and as regards the alcohol component, from polyvalent alcohols, are known. Their molecular weights usually range from about 1000 to 4000.

The unsaturated dicarboxylic acids may be, for example, aliphatic or cycloaliphatic dicarboxylic acids individually or in mixtures. Maleic acid or its anhydride, or fumaric acid, are used preferentially.

The saturated dicarboxylic acids may be, for example, aliphatic or cycloaliphatic or aromatic dicarboxylic acids individually or in mixtures. Preferred are orthophthalic acid or its anhydride and/or isophthalic acid and/or terephthalic acid or dimethylterephthalate and/or tetrahydrophthalic acid and/or adipic acid and/or hexachlorendomethylenetetrahydrophthalic acid.

The polyvalent alcohols are mainly ethylene glycol, propanediol-1,2 and neopentylglycol, mixed, if desired, with lesser amounts of a more than bivalent alcohol, such as trimethylolpropane for example. The unsaturated polyester resins (hereinafter called UP resins) are used in the form of their solutions in a polymerizable monomer, preferably styrene, mainly as casting resins for the production of a wide variety of moldings, an example being the bonding of glass fiber mats or the like. After the addition of radical formers, the UP resin solution, containing a filler if desired, is hardened after shaping, and in some cases post-hardened. Since even at room temperature crosslinking occurs, although slowly, the radical former is not added to the UP resin solution until shortly before it is used. Examples of the radical formers are peroxides, preferably dibenzoylperoxide alone, in the form of a 50% paste, for example, or mixed with tertiary amines such as dimethylaniline.

A very important requirement for the practical application of UP resin solutions is the shelf life of the solutions. In the period between the preparation and the application of the solutions, which may amount to weeks or even months, no alteration of the UP resin solution must occur which would diminish its usefulness. Such undesirable alteration would be, for example, the gel-like stiffening of a UP resin solution during storage at room temperature.

If a UP resin is prepared on the basis of neopentylglycol (100 mole-%) and dimethylterephthalate (26 to 40 mole-%, with reference to the dicarboxylic acid component), isophthalic acid (0 to 14 mole-%) and fumaric acid (60 mole-%) and is dissolved in a proportion of 60 weight parts in 40 weight parts of styrene, it will undergo a gel-like stiffening in 24 to 48 hours at room temperature. The gelling, however, is not due to an incipient cross-linking copolymerization of the resin with the monomer; instead, it is a thixotropic phenomenon that is involved. Despite the fact that the mechanical characteristics of the hardened UP resins are good, especially their Martens thermal stability of shape, of 120° to 125° C., and their thermal stability of shape in accordance with ISO/R 75, A, of 136° to 140° C., the thixotropy of the styrene solution of the UP resin of the above composition makes it entirely unsuitable for use as a casting resin. The shelf life of the styrene solution of the UP resin can be improved by using as the diol component a mixture of at least 25 mole-% ethylene glycol or propanediol-1,2 and no more than 75 mole-% neopentyl glycol. The shelf life which is thereby attained, however, is achieved at the cost of a considerable loss of 10° to 15° C. in the thermal stability of shape of the castings according to the Martens or ISO/R 75 A standards, and of a lowered resistance to hydrolysis.

It has therefore become desirable to provide a solution of unsaturated polyester, particularly a solution thereof in a copolymerizable monomer which possesses good shelf life, does not form a thixotropic solution and provides castings or molded articles having high thermal stability and good resistance to hydrolysis. It is therefore an object of the invention to provide an improved unsaturated polyester which when included in such solution of copolymerizable monomer does not form a thixotropic composition or following copolymerization and setting of the material, form a material which has poor thermal stability.

SUMMARY OF THE INVENTION

The objects of the invention are provided by an improved unsaturated polyester having recurring units of the formula

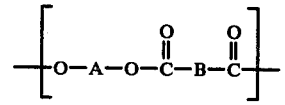

wherein A is the residue of an alcoholic moiety, B is the residue of an acid moiety, which improvement resides in that at least some of the A residues are chloroxylylene containing residues having the formula

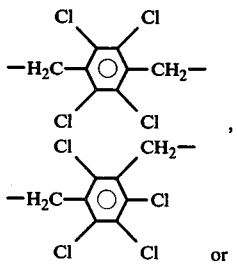

or

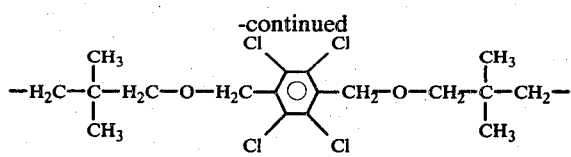

In accordance with the invention, it has been discovered that an improved unsaturated polyester is provided if at least some of those moieties normally provided by the alcohol in the polyester are moieties whose residues have the formulae above. It has been discovered that the resultant unsaturated polyesters when included in a solution of a copolymerizable monomer exhibit exceptional shelf life. Moreover, such solutions can ultimately be formed into molded or cast articles, which articles have a high thermal stability. In fact, the thermal stability of articles formed from solutions containing the unsaturated polyester of the invention is superior to the thermal stability of articles prepared wherein all of the alcoholic moieties are moieties from known alcoholic components.

The unsaturated polyester is prepared generally by utilizing, during the condensation polymerization process, a molar proportion of a compound which supplies one of the three moieties specified above. Since a condensation polymerization is involved, and since the acid component can be supplied by an acid, a lower alkyl ester, an anhydride or an alkali salt of the acid, it is possible also to use instead of an alcohol per se the dichloride thereof and to effect hydrolysis of the dichloride such as in situ by inclusion in the polymerization mixture of a hydrolysis agent such as an alkali metal carbonate. In any event, the resultant unsaturated polyester has between 4 and 20, and preferably between 5 and 15 recurring units of the formula above. Generally speaking, the polymer has a molecular weight between 800 and 4000, preferably between 1000 and 3000 determined through use of a vapor pressure osmometer.

In a preferred embodiment of the invention the unsaturated polyester contains moieties or residues of 2,3,5,6-tetrachloro-p-xylylene glycol and/or 2,3,4,6-tetrachloro-m-xylylene glycol and/or 2,3,5,6-tetrachloro-p-xylylene glycol-bis-(2,2-dimethyl-γ-hydroxypropyl ether). It will be realized that the residue in the final unsaturated polyester can be supplied through the use of such glycol or ether or, alternatively, through the use of the corresponding dichloride e.g. 2,3,5,6-tetrachloro-p-xylylene dichloride or 2,3,4,6-tetrachloro-m-xylylene dichloride. In any event, the final unsaturated polyester contains between 1 and 100 mols of such chloroxylylene containing residue per mol of compound which condenses with the acid containing moiety.

By way of explanation of the terms used herein, the unsaturated polyester has been defined in terms of components thereof rather than in terms of compounds employed to prepare such unsaturated polyester. It is known that polyvalent alcohols can be employed in the preparation of polyesters. The resultant polyester contains a "residue" or "moiety" of the polyvalent alcohol which, of course, is condensed with the acid supplying "residue" in a process by which water or a lower alkanol is given off. The "residue" within the polyester, therefore, is the backbone of the compound and does not take into consideration, in the case of the alcohol residue, the oxygen or hydroxyl groups involved in the condensation. The term "residue" when employed in connection with the acid component is that portion of the acid component excluding the carbonyl and hydroxy groups involved in the condensation. Thus, the alcoholic "residue" of a polyester formed by the condensation of ethylene glycol and terephthalic acid has the formula —CH$_2$—CH$_2$— whereas the acid "residue" has the formula

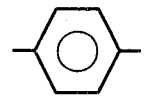

Thus, in the ensuing disclosure where reference is made to the residue of an alcohol or the residue of an acid, it will be realized that that residue itself could have been supplied by the use of the dichloride, in the case of the chloroxylylene containing compound, or by the use of a lower alkyl ester, anhydride, alkali salt or acid itself, such as terephthalic acid, dimethylterephthalate, sodium terephthalate and ortho phthalic acid anhydride.

DESCRIPTION OF SPECIFIC EMBODIMENTS

Unsaturated polyesters preferred in accordance with the invention are constructed on the following basis:

(a) 50 to 97 mol-%, preferably 60 to 94 mol-% of the residue of neopentylglycol, (b) 1 to 30 mol-%, preferably 2 to 20 mol-% of the residue of 2,3,4,6-tetrachloro-m-xylylene glycol, (c) 0 to 49 mol-%, preferably 0 to 38 mol-% of the residue of ethylene glycol or propanediol-1,2, or butanediol-1,3 or butanediol-1,4 or 1,4-bis-(hydroxymethyl)-cyclohexane or mixtures of same, (d) 10 to 70 mol-%, preferably 20 to 50 mol-% of the residue of terephthalic acid, (e) 0 to 30 mol-%, preferably 2 to 20 mol-% of the residue of isophthalic acid, and (f) 30 to 80 mol-%, preferably 40 to 70 mol-% of the residue of fumaric acid, the sum of the diol and dicarboxylic acid components amounting in each case to 100 mol-%.

The polyvalent alcohols used in the polyesters of the invention are the diols known in the preparation of unsaturated polyester resins, such as, for example, ethylene glycol or diethylene glycol or propanediol-1,2 or neopentylglycol or cyclohexanedimethanol, or mixtures thereof, provided that the diol component does not consist of 100 mol-% of the above-named chlorinated xylylene compounds. A mixture of neopentylglycol and at least one of the chlorinated xylylene compounds is used preferentially as the alcohol component.

Instead of the non-halogenated, known diols, mixtures of these diols with more than bivalent alcohols can be used, it being desirable that the amount of the alcohol having more than two hydroxyl groups — trimethylolpropane for example — to be more than 10 mol-% with respect to the total alcohol component.

The acid components used in the unsaturated polyesters of the invention are the dicarboxylic acids known in the preparation of polyester resins, in the anhydride form if desired, or in the form of alkali salts, or, if one or more aromatic dicarboxylic acids are used, their polyester-forming derivatives.

The following are preferred as unsaturated and saturated dicarboxylic acids: maleic acid or its anhydride or alkali salts, fumaric acid or its alkali salts, adipic acid, hexachloroendomethylenetetrahydrophthalic acid, tetrahydrophthalic acid, orthophthalic acid or its anhydride, isophthalic acid, terephthalic acid or its alkyl ester, preferably its dimethyl ester, and hexachlorophthalic acid and the like, or mixtures of the individual components.

In the condensation, the preferred dicarboxylic acid component is a mixture of terephthalic acid or its dimethyl ester with isophthalic acid and fumaric acid.

The use of the halogenated xylylene compounds as diol components in UP resins results in a substantial improvement of the thermal stability of shape of the polyester resins hardened with unsaturated monomers such as styrene, for example. Other unsaturated monomers in which the UP resin of the invention can be dissolved include methylacrylate, methylmethacrylate, acrylonitrile, divinylbenzene and diallylphthalate.

The Martens thermal stability of shape of a UP resin hardened with styrene (60 parts resin and 40 parts styrene) and composed of neopentyl glycol, maleic acid anhdride and phthalic acid anhydride (the two acid components were used in a ratio of 1:1 by weight) ranges, for example, from 65° to 70° C. (see Example 3). However, if instead of neopentyl glycol alone a mixture of neopentyl glycol and 2,3,5,6-tetrachloro-p-xylyleneglycol in a ratio of 1:0.88 by weight is used as the diol component, the Martens temperature increases by more than 25° C. to 96° to 102° C. If, for the sake of comparison, the corresponding amount of the unsubstituted p-xylylene glycol is used, the Martens temperature will be only 78° to 82° C. (see Example 4).

A somewhat lesser improvement of the thermal stability of shape, but one that is similar in tendency, is accomplished by replacing the diols usually used, propanediol-1,2 or neopentyl glycol, with a mixture of neopentyl glycol and 2,3,5,6-tetrachloro-p-xylyleneglycol-bis-(2,2-dimethyl-$\gamma$-hydroxypropyl ether).

An ether of 2,3,5,6-tetrachloro-p-xylyleneglycol, namely 2,3,5,6-tetrachloro-p-xylyleneglycol-bis-($\beta$-hydroxyethyl ether), has been previously used as a diol component for unsaturated polyester resins (cf. F. B. Slezak et al., Ind. Eng. Chem., Vol. 4, No. 4 (1965) page 259), but, as Example 15 for comparison purposes shows, improvements of the thermal stability of shape were not observed.

If, on the other hand, a mixture of neopentyl glycol and 2,3,5,6-tetrachloro-p-xylyleneglycol-bis-(2,2-dimethyl-$\gamma$-hydroxypropyl ether) is used in a ratio of 1:2 by weight (acid components: maleic acid anhydride and phthalic acid anhydride in a weight ratio of 2:1), the Martens temperature is 7° to 80° C. and thus, is about 15° C. higher than it is when a mixture of neopentylglycol and 2,3,5,6-tetrachloro-p-xylyleneglycol-bis-($\beta$-hydroxyethyl ether) is used.

It is also known, in the preparation of combustion-resistant UP resins, to use chlorinated dicarboxylic acids as condensation components, examples being tetrachlorophthalic acid anhydride or hexachloroendomethylenetetrahydrophthalic acid (HET acid). To reduce combustibility, these compounds have to be copolymerized in amounts enabling the chlorine content of the end product to increase to over 20% by weight. Increasing the chlorine content to more than 30% by weight is virtually impossible, because the percentage of the unsaturated acid in such a case is so small that the Martens temperature is extremely low. A self-extinguishing property is achieved, but has to be accomplished at the cost of an impairment of the mechanical characteristics. However, if the chlorine content is brought in through the diol component and the chlorinated xylene compounds of the invention are used, even in a mixture with at least one other diol, styrene-hardened UP resins are obtained which, with a chlorine content of about 26% by weight, are resistant to combustion, but at the same time also have good thermal stability of shape. Self-extinguishing resins can be produced, for example, by providing a chlorine content of at least 30 weight percent. Generally speaking, the UP resins of the invention can be distinguished from prior art UP resins in that they have a chlorine content of about 1 and 45%, preferably between 3 and 40%. More especially, they can be distinguished because the A moiety thereof contains between 2 and 60 weight percent of chlorine. Prior art resins are virtually free of chlorine on the A moiety or residue.

Provision can also be made for copolymerizing phenylphosphonic acid into the products of the invention, in such an amount, for example, that the hardened resin will contain about 1% phosphorus by weight. In this manner, too, combustion resistant or self-extinguishing products can be achieved.

Surprisingly, the polyesters of the invention, when dissolved in a copolymerizable monomer, preferably styrene, have an excellent shelf life.

Therefore, polyester resin solutions containing an unsaturated polyester resin in amounts between 20 and 80 percent by weight, preferably between 40 and 70 wt.-%, and a copolymerizable monomer, especially styrene, are additional subject matter of the invention.

The polyester resin solutions of the invention are capable of storage and use for months without alteration. For example, a solution in styrene of a resin composed on a basis of neopentylglycol as the alcohol component, plus dimethylterephthalate (26 to 40 mol-%, with respect to the dicarboxylic acid component), isophthalic acid (0 to 14 mol-%) and fumaric acid (60 mol-%), and dissolved in a proportion of 60 parts by weight to 40 parts of styrene by weight, will stiffen in the manner of a gel after 24 to 48 hours of standing at room temperature. Surprisingly, an excellent shelf life is achieved in UP resin solutions if, instead of neopentylglycol as the alcohol component, a mixture of neopentylglycol and, for example, 2,3,4,6-tetrachloro-m-xylyleneglycol is used.

The polyester resin solution in styrene in accordance with the invention is capable of storage and use for months without alteration. This good shelf life is not achieved at a cost of the Martens thermal stability of shape of the hardened polyester resins as it is in the polyester solutions that have been known hitherto. Instead, the thermal stability of shape is further improved, while at the same time good resistance to hydrolysis is retained to the full extent.

The composition of the alcohol component that is most favorable as regards shelf life and mechanical characteristics is 60 to 97 mol-%, preferably 70 to 94 mol-%, of neopentylglycol and 3 to 40 mol-%, preferably 6 to 30 mol-%, of tetrachloro-m-xylyleneglycol (the sum of the polyvalent alcohols used is 100 mol-%). Without impairing the good characteristics of the hardened castings, still other bivalent alcohols can be used as additional alcohol components, such as, for example, ethyleneglycol, propanediol-1,2, butanediol-1,3, butanediol-1,4 or 1,4-bis-(hydroxymethyl)-cyclohexane, in amounts between 0 and 30 mol-%, with reference to the total amount of the alcohol component. A part of the diols of the prior art, preferably up to about 10 mol-%, can be replaced by a more than bivalent alcohol, such as trimethylolpropane, for example.

Another feature of the invention resides in a method of preparing unsaturated polyester resins dervcied from unsaturated and in some cases saturated dicarboxylic acids as regards the acid component, and from bivalent alcohols or mixtures thereof with more than bivalent alcohols as regards the alcohol component, by condensation, preferably by fusion condensation of the components, in the presence of inhibitors if desired, which is characterized in that 1 to 100 mol-%, preferably 2 to 75 mol-%, of the alcohol component used (with respect to the total amount of the alcohol component), consists of 2,3,5,6-tetrachloro-p-xyleneglycol and/or 2,3,4,6-tetrachloro-m-xyleneglycol and/or 2,3,5,6-tetrachloro-p-xyleneglycol-bis-(2,2-dimethyl-γ-hydroxypropyl ether).

It will be understood that the manipulative steps by which unsaturated polyesters are prepared do not differ materially from the manipulative steps by which known polyesters, especially known unsaturated polyesters, have been prepared. The condensation conditions will depend upon the specific mode of condensation desired and the nature of the reactants. For instance, if condensation is to be a transesterification reaction followed by a polycondensation, it is desirable to employ an inert atmosphere. In any event, conditions are maintained whereby the functional groups on the alcoholic moiety and the functional groups on the acid supplying moiety are caused to condense to yield water or, in the case of a transesterification, an alcohol. The by-product is usually removed whereby there is obtained a material which can be subjected to polycondensation. The final polymer will generally have a molecular weight of between 800 and 4000 as determined by a vapor pressure osmometer. The principal characterizing feature of the process of the invention resides in the fact that a portion of the A moiety is supplied by one of the named chloroxylylene containing compounds, including dichloride or ether. This, instead of utilizing a tetrachloro-p-xyleneglycol or tetrachloro-m-xyleneglycol, the corresponding xylylene dichlorides as well as the alkali salts of the unsaturated dicarboxylic acid or dicarboxylic acid mixtures can be employed.

Since on the one hand the diols can be produced from tetrachloro-p-xylylenedichloride or tetrachloro-m-xylylenedichloride, as the case may be, for example by either direct hydrolysis of the dichlorides (e.g., at 150° C. under pressure with aqueous soda solution), or for example, by hydrolysis of the bis-acetates obtainable therefrom with sodium acetate, and, on the other hand, the direct esterification of the dichlorides can be performed with the alkali salts of the unsaturated acids, with the release of alkali chloride, the above-named synthesis can be avoided and, instead of the xyleneglycols used in accordance with the invention, the corresponding tetrachloroxylylenedichlorides can be used directly for the condensation. The alkali salts of the unsaturated acids can likewise be produced directly in the condensation mixture from the acids and, for example, alkali carbonate. The alkali chloride that forms during the esterification and remains in the UP resin can easily be separated, if necessary, by centrifugation or filtration after dissolving the resin in styrene.

The 2,3,5,6-tetrachloro-p-xyleneglycol-bis-(2,2-dimethyl-γ-hydroxypropyl ether) used in accordance with the invention can be obtained from tetrachloro-p-xylylenedichloride and neopentylglycol in an alkaline medium via the sodium salt of neopentylglycol with the removal of NaCl, or by direct condensation of tetrachloro-p-xylylenedichloride with neopentylglycol with the removal of HCl.

The UP resins are prepared preferably by the fusion polycondensation method, although the described polyesters can also be prepared by polycondensation in solution or by azeotropic polycondensation. The procedure may be, for example, as follows:

If dicarboxylic acid esters such as dimethylterephthalate or dimethylisophthalate are available as acid components, they are first transesterified with the diols, and not until the transesterification has been completed are they polycondensed with the rest of the acid components. The transesterification is performed in a known manner in the temperature range from 140° C. to 200° C., preferably 150° C. to 180° C., using known transesterification catalysts such as $PbO_2$, zinc acetate or manganese acetate. After the addition of the rest of the dicarboxylic acid components, especially maleic acid anhydride and/or fumaric acid, the polycondensation is completed to the desired molecular weight by increasing the temperature to 240° C. maximum, preferably 200° to 220° C. The end point of the polycondensation can easily be determined on the basis of a calibration curve (the Brookfield viscosity of the molten UP resins at the terminal condensation temperature as a function of the molecular weight). Owing to the oxidation sensitivity of the reactants, especially the alcohol components, at the high condensation temperature, both the transesterification and the polycondensation are performed under an inert gas atmosphere.

If saturated dicarboxylic acids are also used as reactants, it has been found desirable first to add and copolymerize the saturated dicarboxylic acids and to add the unsaturated dicarboxylic acids as the last reactants. This order of procedure has advantages, especially when isophthalic acid and fumaric acid are used, for UP resins are obtained with a low percentage that is insoluble in styrene, and the thermally more sensitive unsaturated dicarboxylic acids are not exposed for too long to the high condensation temperature.

In cases in which the tetrachloroxylylenedichlorides are esterified with the alkali salts of the unsaturated dicarboxylic acids, the alkali salts do not need to be produced in a separate reaction. Instead, it is sufficient to add an amount of alkali carbonate, preferably soda, equivalent to the tetrachloroxylylenedichloride (1 mol of alkali carbonate per mol of tetrachloroxylylenedichloride), together, in some cases, with a small amount of water (when maleic acid anhydride is used as an unsaturated dicarboxylic acid component), in order to perform the hydrolysis of the anhydride to the acid, the transposition of the dicarboxylic acid with soda to form the sodium salt, and the reaction of the sodium salt with the tetrachloroxylylenedichloride with the formation of the ester. The formation of ester from alkyl halide and the alkali salt of the dicarboxylic acid in this case takes place at lower temperatures (ranging from 120° C. to 150° C.) than would be necessary for the esterification of alcohol and acid with the production of water.

In the event of the simultaneous presence of diols as reaction components, the temperature must be increased to 180° C. to 230° C. to complete the esterification that takes place with the production of water.

The alkali chloride that forms can easily be separated, if necessary, by centrifuging or filtering the styrene solution of the UP resin. If the alkali chloride remains in the UP resin solution, this will not result in any disadvantages in the hardening process, nor will the mechanical properties of the casting be impaired to any noticeable extent, aside from a slight turbidity.

In order to more fully illustrate the nature of the invention and the manner of practicing the same, the following Examples are presented:

EXAMPLES

The invention will be further explained with the aid of examples.

The values given in the Examples were determined on the basis of the following standards:
Vicat temperature: DIN 53,460, Method B
Bending strength: DIN 53,452
Impact strength: DIN 53,453
Notch impact strength: DIN 53,453
Hardness, ball test: DIN 53,456
Martens temperature: DIN 53,458
ISO/R 75 A: DIN 53,461

EXAMPLE 1

(a) Preparation of 2,3,5,6-tetrachloro-p-xylyleneglycol-bis-(2,2-dimethyl-γ-hydroxypropylether), hereinafter called Product III In a 2-liter round flask equipped with stirrer and reflux condenser, 208 g (2 moles) of neopentylglycol and 80 g (2 moles) of solid sodium hydroxide were placed under a weak current of nitrogen, and the mixture was slowly heated. At 160° C. a clear molten mixture was obtained. In a temperature range between 130° and 150° C., 250 g (0.8 mole) of tetrachloro-p-xylylenedichloride were added in portions over a period of 2 hours.

The temperature was then increased to 160° C. and the mixture was refluxed for 8 hours. The mixture was stirred while still hot into water, whereupon the desired Reaction Product III precipitated as a plastic mass together with a lesser amount of tetrachloro-p-xylyleneglycol. After washing with water it was dissolved in acetone. The part that was soluble in acetone was precipitated by pouring it into water, and it was washed and dried. It was the desired product, 2,3,5,6-tetrachloro-p-xylyleneglycol-bis-(2,2-dimethyl-γ-hydroxypropylether). It amounted to 232 g of III, which corresponded to 65% of the theory (with respect to tetrachloro-p-xylylenedichloride).

| Elemental Analysis: | C | H | Cl |
|---|---|---|---|
| Calculated: | 48.2 | 5.8 | 31.6 |
| Found: | 48.5 | 5.3 | 32.9 |

Molecular weight (in tetrahydrofuran in the vapor pressure osmometer): Calculated 448; found 455
Hydroxy number: calculated 250; found 241.

The fraction that was insoluble in acetone was dissolved in DMF and precipitated in water, washed and dried. It amounted to 42.6 g of tetrachloro-p-xylyleneglycol, which corresponded to 19% of the theory (with respect to tetrachloro-p-xylylenedichloride).

| Elemental Analysis: | C | Cl |
|---|---|---|
| Calculated: | 34.7 | 51.5 |
| Found: | 35.1 | 50.8 |

Molecular weight (vapor pressure osmometer): Calculated 276; found 263.
Hydroxy number: calculated 405; found 403.
Ratio of the methylene protons to the hydroxyl protons (nuclear magnetic resonance) = 4.06:2.

Of the 0.8 mole of tetrachloro-p-xylylenedichloride put in, 65% (0.52 mole) was transformed to 2,3,5,6-tetrachloro-p-xylyleneglycol-bis(2,2-dimethyl-γ-hydroxypropylether) and 19% (0.16 mole) was transformed to 2,3,5,6-tetrachloro-p-xylyleneglcyol.

(b) Preparation of 2,3,5,6-tetrachloro-p-xylyleneglycol-bis-(2,2-dimethyl-γ-hydroxypropylether)

In a reaction vessel equipped with a stirrer and a reflux condenser, 416 g (4 moles) of neopentylglycol was melted at 150° C. and 250 g (0.8 mole) of tetrachloro-p-xylenedichloride was added portion by portion. After the addition of 2 g of magnesium chips, the reaction mixture was stirred for 4 hours at 150° to 170° C. and then for 8 hours at 180° C., while a weak current of nitrogen was passed through the vessel to carry out of the system the hydrogen chloride that formed. After this period no more hydrogen chloride gas was formed and the condensation had ended. The clear reaction mixture was stirred, while still hot, into an excess of water and the precipitated reaction product was washed with water. It was dissolved in acetone for refinement and precipitated in an excess of water, washed and dried.

329 g of 2,3,5,6-tetrachloro-p-xylyleneglycol-bis(2,2-dimethyl-γ-hydroxypropylether) was obtained. The yield was 92% of the theory, with respect to the tetrachloro-p-xylylenedichloride.

| Elemental Analysis: | C | H | Cl |
|---|---|---|---|
| Calculated | 48.2 | 5.8 | 31.6 |
| Found | 48.7 | 5.6 | 32.4 |

Molecular Weight (in the vapor pressure osmometer): Calculated 448; found 439
Hydroxyl Number: Calculated 250; found 243.

The ratio between the hydroxyl units, the neopentylglycol units and the tetrachloro-p-xylylene units in the reaction product amounted to 2:2.04:1.09, as determined by quantitative nuclear magnetic resonance.

EXAMPLE 2

104 g (1 mole) of neopentylglycol, 91 g (0.33 mole) of tetrachloro-p-xylyleneglycol and 75.5 g (0.77 mole) of maleic acid anhydride and 82.9 g (0.56 mole) of phthalic acid anhydride were placed in a reaction vessel equipped with a stirrer. After the addition of 35 mg of hydroquinone as inhibitor, the mixture was externally heated while a weak current of nitrogen was passed through the vessel, and the temperature was raised over a period of 3 hours to 190° C. At 190° C., the polycondensation was continued for another 5 hours to completion, and the viscous polyester melt was poured onto a metal plate. The UP resin had a molecular weight (vapor pressure osmometer) of 1700 to 1800. The chlorine content was approximately 14% by weight. The UP resin was dissolved in styrene (60 weight-parts of polyester in 40 weight-parts of styrene) and the UP resin solution was hardened for 2 hours at 40° C. in a mold with 2 wt.-% of dibenzoylperoxide paste (50%) and 0.025 volume-percent of dimethylaniline (as a 10% solution in styrene), and was then cured for 4 hours at 120° C. Colorless, transparent plates 4 mm thick were obtained, which had the following characteristics:

Vicat temperature: 160°–170° C.
Martens temperature* 98° C.
Impact strength* 9.3 cmkp/cm²
Notch impact strength 1.0 cmkp/cm²
Bending strength 900 kp/cm²
Hardness, ball test (10 sec.) 1480 kp/cm²
*Measured on a standard size specimen kp = kiloponds

EXAMPLE 3

(Example for purposes of comparison, without tetrachloro-p-xylyleneglycol)

Under polycondensation conditions similar to Example 2, a UP resin was prepared from 138 g (1.33 moles) of neopentylglycol, 75.5 g (0.77 mole) of maleic acid anhydride and 82.9 g (0.56 mole) of phthalic acid anhydride with a molecular weight (determined by a vapor pressure osmometer) of 1850 to 1900, and 60 parts thereof by weight were dissolved in 40 parts by weight of styrene. After hardening (with 2 wt.-% dibenzoyl peroxide paste (50%) and 0.025 vol.-% of dimethylaniline) and then curing at 120° C., a transparent, colorless, 4 mm thick plate was obtained having the following properties:

Vicat temperature: 140°–150° C.
Martens temperature*: 67° C.
Impact strength*: 8.7 cmkp/cm²
Notch impact strength: 1.0 cmkp/cm²
Bending strength: 870 kp/cm²
Hardness, ball test, 10 sec.: 1390 kp/cm²
*Measured on a standard size specimen.

The thermal stability of shape in accordance with the Vicat and Martens tests was thus considerably below that of the UP resin containing tetrachloro-p-xylyleneglycol.

EXAMPLE 4

(Example for purposes of comparison, using p-xylyleneglycol instead of tetrachloro-p-xylyleneglycol)

Under condensation conditions similar to Example 2, a UP resin having a molecular weight of 1900 to 1950 was prepared from 104 g (1 mole) of neopentylglycol, 45.5 g (0.33 mole) of p-xylyleneglycol, 75.5 g (0.77 mole) of maleic acid anhydride and 82.9 g (0.56 mole) of phthalic acid anhydride, and 60 parts by weight thereof were dissolved in 40 parts by weight of styrene. After hardening followed by curing under the same conditions as in Example 2, transparent, colorless plates were obtained having the following:

Vicat temperature: 153°–158° C.
Martens temperature*: 81° C.
Impact strength*: 7.8 cmkp/cm²
Bending strength: 890 kp/cm²
Hardness, ball test, 10 sec.: 1420 kp/cm²
*Measured on standard size specimen.

The replacement of the tetrachloro-p-xylylene diol with p-xylylene diol thus permits a reduction of the Martens temperature by almost 20° C.

EXAMPLE 5

156 g (1.5 moles) of neopentylglycol and 82.8 g (0.3 mole) of tetrachloro-p-xylyleneglycol were transesterified with 116.4 g (0.6 mole) of dimethylterephthalate between 150° and 180° C., with the addition of 0.1 g of lead dioxide as the transesterification catalyst, and then 58.8 g (0.6 mole) of maleic acid anhydride and 69.6 g (0.6 mole) of fumaric acid was added together with 60 mg of hydroquinone, and polycondensed between 150° and 200° C. until a molecular weight of 1800 (vapor pressure osmometer) was attained. The resin had a chlorine content of about 10% by weight. The UP resin was dissolved in styrene in a ratio of 60 to 40 parts by weight and hardened for 2 hours at 35° C. with 2 wet.-% dibenzoylperoxide paste (50%) and 0.03 vol.-% of dimethylaniline (as a 10% solution in styrene), and then it was cured for 2 hours at 135° C. Colorless, transparent plates were obtained with the following characteristics:

Vicat temperature: more than 200° C.
Martens stability of shape*: 122° C.
Stability of shape in accordance with ISO/R 75, A: 139° C.
Impact strength*: 9.6 cmkp/cm²
Hardness, ball test, 10 sec.: 1560 kp/cm²
*Measured on a standard size specimen.

EXAMPLE 6

(Example for purposes of comparison, using no tetrachloro-p-xylyleneglycol)

187.2 g (1.8 moles) of neopentylglycol was transesterified with 116.4 g (0.6 mole) of dimethylterephthalate in the presence of 0.1 g of PbO₂ between 140° and 180° C., and then 58.8 g (0.6 mole) of maleic acid anhydride and 69.6 g (0.6 mole) of fumaric acid were added together with 60 mg of hydroquinone, and the mixture was polycondensed between 160° and 200° C. up to a molecular weight of 1700 to 1750 (vapor pressure osmometer).

The UP resin was dissolved in styrene in a ratio of 60 parts to 40 parts of styrene, by weight, and hardened and then cured under the same conditions as in Example 5. Transparent, colorless plates 4 mm thick were obtained having the following characteristics:

Vicat temperature: 198° C.
Martens thermal stability of shape*: 101° C.
Thermal stability of shape per ISO/R 75, A: 119° C.
Impact strength*: 7.9 cmkp/cm²
Hardness, ball test, 10 sec.: 1490 kp/cm²
*Measured on a standard size specimen.

Examples 5 and 6 show that the use of tetrachloro-p-xylyleneglycol as one of the diol components (17 mole-%; the balance is neopentylglycol) in the above UP resin formula causes the thermal stability of shape of the hardened castings, as determined by the Martens method or pursuant to ISO/R 75, A, to increase by about 20° C., and also results in an improvement of the Vicat temperature, ball test hardness and even the impact strength.

EXAMPLE 7

(Use of tetrachloro-m-xylyleneglycol)

165.6 g (0.6 mole) of tetrachloro-m-xylyleneglycol, 312 g (3 moles) of neopentylglycol and 23 3 g (1.2 moles) of dimethylterephthalate were transesterified for 2 hours at 160°–180° C. after the addition of 0.05 g of PbO₂. Then 130 g (1.2 moles) of fumaric acid and 118 g (1.2 moles) of maleic acid anhydride plus 100 mg of hydroquinone were added and the mixture was polycondensed at a temperature increasing slowly up to 220° C., until a molecular weight of 2000 is achieved.

The UP resin was dissolved in styrene in a ratio of 60 parts to 40 parts of styrene by weight, and hardened in a mold with 2 wt.-% of a 50% dibenzoylperoxide paste and 0.025 vol.-% of dimethylaniline (as a 10% solution in styrene) at 40° C. for 2 hours, and then cured for two hours at 135° C. Colorless, transparent plates 4 mm thick were obtained having the following mechanical characteristics:

Vicat temperature: >200° C.

Martens thermal stability of shape*: 112° C.

Thermal stability of shape pursuant to ISO/R 75, A: 128° C.

Impact strength*: 7.4 cmkp/cm$^2$

*Measured on a standard size specimen.

EXAMPLE 8

104 g (1 mole) of neopentylglycol, 115.9 g (0.37 mole of tetrachloro-p-xylylenedichloride, 72.5 g (0.74 mole) of maleic acid anhydride, 54 g (3 moles) of water, 39.2 g (0.37 mole) of sodium carbonate and 30 mg of hydroquinone were placed in a reaction vessel equipped with a stirrer and a gas feeding tube, heated over a period of 3 hours to 170° C. under a weak current of nitrogen, and esterified at this temperature for 6 hours. Then 91.7 g (0.62 mole) of phthalic acid anhydride were added, and, after heating to 190° C., polycondensation was performed until a molecular weight of 1400 was attained. The UP resin contains about 14.5 wt.-% of organically bound chlorine. The UP resin was dissolved in styrene in a ratio of 60 parts resin to 40 parts styrene by weight, and a portion of the UP resin solution, which was turbid due to the presence of finely divided sodium chloride, was centrifuged. Both the solution freed of NaCl by centrifugation and the solution containing NaCl were hardened at 40° C. in a mold with 2 wt.-% of a 50% dibenzoylperoxide paste and 0.03% dimethylaniline by volume (as a 10% solution in styrene), and cured for 2 hours at 120° C. In the case of the NaCl-free resin solution, transparent plates 4 mm thick were obtained having the following characteristics:

Vicat temperature: 167° C.

Thermal stability of shape Martens method*: 105° C.

Method of ISO/R 75, A: 119° C.

Impact strength: 6.9 kpcm/cm$^2$

Ball test hardness (10 sec.): 1520 kp/cm$^2$

*Measured on a standard size specimen.

Hardening of the UP resin solution containing NaCl resulted in opaque plates 4 mm thick having the following characteristics:

Vicat temperature: 182° C.

Thermal stability of shape Martens method*: 107° C.

Method of ISO/R 75, A: 117° C.

Impact strength:* 5.7 cmkp/cm$^2$

Ball test hardness (10 sec.): 1560 kp/cm$^2$

*Measured on a standard size specimen.

EXAMPLE 9

33.4 g (0.32 mole) of neopentylglycol, 37.2 g (0.12 mole) of tetrachloro-p-xylylenedichloride, 32.8 g (0.24 mole) of maleic acid, 12.7 g (0.12 mole) of sodium carbonate and 0.08 g of piperidine (as catalyst for the cis-trans isomerization of the maleic acid to fumaric acid) were esterified up to 170° C. after the addition of 10 mg of hydroquinone, in the same manner as in Example 8, and after the addition of 29.6 g (0.2 mole) of phthalic acid anhydride, they were polycondensed to a molecular weight of 1700 (final condensation temperature 200° C.).

The UP resin contains approximately 14.5% by weight of organically bound chlorine. It was dissolved in a ratio of 60 parts by weight to 40 parts by weight of styrene, part of the solution was separated from the sodium chloride by centrifugation, and both solutions were hardened in a mold in the same manner as in Example 8 to form 4 mm thick plates.

| Characteristics: | | | |
|---|---|---|---|
| Vicat temperature: | 194° C | 183° C | (centrifuged specimen) |
| Martens temperature:* | 116° C | 113° C | " |
| ISO/R 75, A: | 131° C | 129° C | " |
| Impact strength:* | 7.2 cmkp/cm$^2$ | 6.0 cmkp/cm$^2$ | " |

*Measured on standard size specimens.

EXAMPLE 10

In the same manner as in Example 8, a UP resin having a molecular weight of 1460 was prepared from 28 g (0.27 mole) of neopentylglycol, 28.1 g (0.09 mole) of tetrachloro-m-xylylenedichloride, 22.8 g (0.21 mole) of maleic acid anhydride, 9.5 g (0.09 mole) of sodium carbonate and 9 g (0.5 mole) of water plus 22.2 g (0.15 mole) of phthalic acid anhydride, and, after being dissolved in styrene (60 wt.-parts of resin to 40 wet.-parts of styrene), was hardened with 2 wt.-% of a 50% paste of dibenzoylperoxide and 0.03% by volume of dimethylaniline. Opaque plates 4 mm thick were obtained, having the following characteristics:

Vicat temperature: 173° C.

Martens temperature*: 89° C.

ISO/R 75, A: 109° C.

Impact strength*: 7.6 kpcm/cm$^2$

*Measured on a standard size specimen.

EXAMPLE 11

(Example for purposes of comparison, using p-xylylenedichloride)

In the same manner as in Example 8, a UP resin having a molecular weight (vapor pressure osmometer) of 1530 was prepared from 28 g (0.27 mole) of neopentylglycol, 15.8 g (0.09 mole) of p-xylylenedichloride, 22.8 g (0.21 mole) of maleic acid anhydride, 9.5 g (0.09 mole) of sodium carbonate, 9 g (0.5 mole) of water and 22.2 g (0.15 mole) of phthalic acid anhydride, and, after dissolution in styrene (60 weight-parts resin to 40 weight parts styrene), was hardened with dibenzoylperoxide and dimethylaniline. Opaque plates 4 mm thick were obtained, having the following characteristics:

Vicat temperature: 158° C.

Martens temperature*: 79° C.

ISO/R 75, A: 93° C.

Impact strength*: 6.7 cmkp/cm$^2$

*Measured on a standard size specimen.

EXAMPLE 12

127.05 g (0.27 Mole) of propanediol-1,2, 28.1 g (0.09 mole) of tetrachloro-p-xylylenedichloride, 22.8 g (0.21 mole) of maleic acid anhydride, 9.5 g (0.09 mole) of sodium carbonate and 9 g (0.5 mole) of water were esterified, after the addition of 10 mg of hydroquinone, at a temperature slowly increasing to 170° C.

After the addition of 22.2 g (0.15 mole) of phthalic acid anhydride, polycondensation was performed while increasing to a final temperature of 190° C., until a molecular weight of 1650 was attained. The UP resin was dissolved in styrene in a ratio of 65 parts by weight to 35 parts by weight of styrene, and hardened in a moled with dibenzoyl peroxide and dimethylaniline. Opaque plates 4 mm thick are obtained, having a Vicat temperature of 159° C., a Martens temperature of 104° C. and an inpact strength of 6.4 cmkp/cm$^2$.

EXAMPLE 13

104 g (1 mole) of neopentylglycol was placed together with 0.01 g of $PbO_2$ (transesterification catalyst) in a reaction vessel and heated to 170° C. Under a slow current of nitrogen, 68 g (0.5 mole) of benzoic acid methyl ester was added drop by drop, with stirring, over a period of 90 minutes and the reaction mixture was held for another hour at 170° C. After the transesterification, 98 g (1 mole) of maleic acid anhydride, 156 g (0.5 mole) of tetrachloro-p-xylylenedichloride, 53 g (0.5 mole) of sodium carbonate and 36 g (2 moles) of water were added and the reaction mixture was stirred at 120° C. for one hour. Then the temperature was increased over a period of 2 hours to 190° C. and condensation was performed for 3 hours at this temperature. The UP resin was dissolved in styrene in a ratio of 65 parts by weight to 35 parts by weight of styrene, and hardened in a mold with dibenzoylperoxide and dimethylaniline. Opaque plates 4 mm thick were obtained, having a Vicat temperature of 146° C., a Martens thermal stability of shape of 68° C. and a stability of shape pursuant to ISO/R 75, A, of 79° C. and an impact strength of 6.5 kpcm/cm².

EXAMPLE 14

154 g (1.4 mole) of neopentylglycol, 311 g (0.7 mole) of tetrachloro-p-xylyleneglycol-bis-(2,2-dimethyl-γ-hydroxypropylether), 89 g (0.6 mole) of phthalic acid anhydride and 147 g (1.5 moles) of maleic acid anhydride were placed in a reaction vessel, 80 mg of hydroquinone were added and, under a slow current of nitrogen, the mixture was polycondensed at a temperature increasing over a period of 3 hours to 200° C. and continuing for an additional 3.5 hours until a molecular weight of b 1570 (vapor pressure osmometer) was attained.

The UP resin was dissolved in styrene at a ratio of 55 parts by weight to 45 parts by weight of styrene, and the solution was hardened in a moled with 2 wt.-% of 50% dibenzoyl peroxide paste and 0.03 vol.-% ofdimethylaniline (as a 10% solution in styrene) to form transparent plates 4 mm thick having the following characteristics:

Vicat temperature: 163° C.
Martens temperature*: 77° C.
Impact strength*: 5.8 L cmkp/cm²
*Measured on a standard size specimen.

EXAMPLE 15

(Example for purposes of comparison, using tetrachloro-p-xylyleneglycol-bis-(β-hydroxyethylether)

77 g (0.7 mole) of neopentylglycol, 155 g (0.38 mole) of tetrachloro-p-xylyleneglycol-bis-(β-hydroxyethylether), 44.5 g (0.3 mole) of phthalic acid anhydride and 73.5 g (0.75 mole) of maleic acid anhydride were placed together with 40 mg of hydroquinone in a reaction vessel and, under a slow current of nitrogen, the mixture was polycondensed at a temperature rising slowly to 200° C., until a molecular weight of 1650–1700 (vapor pressure viscosimeter) was attained. The UP resin was dissolved in styrene in a ratio of 55 wt.-parts to 45 wt.-parts of styrene and hardened to a mold with 2 wt.-% of a 50% dibenzoylperoxide paste and 0.03 vol.-% of dimethylaniline to form 4 mm thick plates having the following characteristics:

Vicat temperature: 144° C.
Martens temperature*: 61° C.
Impact strength*: 4.8 cmkp/cm²
*Measured on a standard size specimen.

A comparison of Examples 14 and 15 will show that, in a formula that is otherwise the same, the replacement of the tetrachloro-p-xylyleneglycol-bis-(β-hydroxyethylether) by the same amount of tetrachloro-p-xylyleneglycol-bis-(2,2-dimethyl-γ-hydroxypropylether) increases the Vicat thermal stability of shape by about 20° C. and the Martens thermal stability of shape by about 15° C., with a slight improvement of the impact strength.

EXAMPLE 16

A UP resin having a molecular weight of 1430 (vapor pressure osmometer) was prepared from 58 g (0.56 mole) of neopentylglycol, 124.4 g (0.28 mole) of tetrachloro-p-xylyleneglycol-bis-(2,2-dimethyl-γ-hydroxypropylether), 29.6 g (0.2 mole) of phthalic acid anhydride and 74.4 g (0.64 mole) of fumaric acid was dissolved in styrene (50 wt.-parts of resin in 50 wt.-parts of styrene), and hardened with 2 wt.-% of a 50% dibenzoylperoxide paste and 0.03 vol.-% of dimethylaniline. Transparent plates 4 mm thick were obtained, having the following characteristics:

Vicat temperature: 198° C.
Martens temperature*: 108° C.
Impact strength*: 6.1 cmkp/cm²
*Measured on a standard size specimen.

EXAMPLE 17

93.6 g (0.9 mole) of neopentylglycol and 27.6 g (0.1 mole) of tetrachloro-m-xylyleneglycol were transesterified with 69.8 g (0.36 mole) of dimethylterephthalate with the addition of 85 mg of lead dioxide, for 1.5 hours at a temperature range of 160°–180° C.

Then 6.64 g (0.04 mole) of isophthalic acid and 45 mg of hydroquinone were added, and the mixture was esterified for 1 hour at 180° C. and for 1 hour at 200° C. Then 69.6 g (0.6 mole) of fumaric acid was added and the mixture was polycondensed for 1 hour at 200° C. and 5 hours at 220° C.

A transparent, unsaturated polyester resin was obtained having a molecular weight of 2100 (vapor pressure osmometer). The UP resin was dissolved in styrene in a ratio of 60 wt.-parts to 40 wt.-parts of styrene. A solution was obtained which is only very slightly turbid, having a pouring time of 497 seconds at 24° C. in the DIN beaker (4 mm nozzle).

A portion of the UP resin solution was hardened in a mold with 2 wt.-% of a 50% dibenzoylperoxide paste and 0.03 vol.-% of dimethylaniline, at 40° C., and cured for 4 hours at 135° C.

Transparent, colorless plates 4 mm thick were obtained having the following characteristics:

Vicat temperature: >200° C.
Thermal stability of shape Martens*: 128° C.
ISO/R 75, A: 142° C.
Impact strength*: 6.6 cmkp/cm²
*Measured on standard size specimens.

Two other portions of the UP resin solution were stored in the closed vessel at room temperature (20°–23° C.) and at 35° C., over a long period of time. Neither specimen showed any external alteration even after 64 days; the solutions were still fluid enough to pour. The pouring time at 24° C. in the DIN beaker (4 mm nozzle) was 522 seconds for the UP resin solution stored at room temperature, and 538 seconds for the one stored at 35° C.

EXAMPLE 18

(For Comparison Purposes)

104 g (1 mole) of neopentylglycol was transesterified for 1 hour at 180° C. in the presence of lead dioxide, with 69.8 g (0.36 mole) of dimethylterephthalate; then 6.64 g (0.04 mole) of isophthalic acid and 30 mg of hydroquinone were added and the mixture was condensed for 1 hour at 180° C. and one hour at 200° C. After the addition of 69.6 g (0.6 mole) of fumaric acid, it was polycondensed for one hour at 200° C. and 4 hours at 220° C. A UP resin was obtained having a molecular weight of 2050 (vapor pressure osmometer) which was dissolved in styrene in a ratio of 60 weight parts to 40 weight parts of styrene. A turbid UP resin solution was obtained having a pouring time of 484 seconds at 24° C. in the DIN beaker (4 mm nozzle). A portion of the solution was hardened in a mold at 40° C. immediately after the dissolution, using 2 wt.-% of a 50% dibenzoyl peroxide paste and 0.03 vol.-% of dimethylaniline, and cured at 135° C. for 4 hours. Slightly turbid plates 4 mm thick were obtained having the following characteristics:

Vicat temperature: >200° C.
Thermal stability of shape Martens*: 124° C.
ISO/R 75, A: 138° C.
Impact strength*: 6.4 cmkp/cm$^2$
*Measured on a standard size specimen.

Two other portions of the UP resin solution were stored in the closed vessel at room temperature (20–23° C.) and at 35° C. After only 2 days, both specimens were opaque and gelled and were no longer fluid. The gelling is based not on a cross-linking copolymerization of the styrene with the fumaric ester double bonds of the UP resin, because intense mixing with a high-speed stirrer quickly restores the resin to a fluid, opaque solution, which nevertheless stiffens again within 36 hours.

A UP resin having such a poor shelf life would not be usable for practical purposes.

EXAMPLE 19

72.8 g (0.7 mole) of neopentylglycol, 15.5 g (0.25 mole) of ethylene glycol, 13.8 g (0.05 mole) of tetrachloro-m-xylyleneglycol and 69.8 g (0.36 mole) of dimethylterephthalate were transesterified for 1 hour at 180° C. after the addition of 0.082 g of lead dioxide as catalyst. Then 6.64 g (0.04 mole) of isophthalic acid and 0.045 g of hydroquinone were added and the mixture was esterified for 1 hour at 180° C. and 1 hour at 200° C. After the addition of 69.65 g (0.6 mole) of fumaric acid, the mixture was esterified for an additional hour at 200° C. and then polycondensed at 220° C. until a molecular weight of 2000 (vapor pressure osmometer) was attained.

The UP resin was dissolved in a ratio of 60 parts by weight to 40 parts by weight of styrene, and a portion of the solution is hardened in a mold with 2 wt.-% of a 50% dibenzoylperoxide paste and 0.03 vol.-% of dimethylaniline at 40° C., and cured for 4 hours at 135° C. Transparent, colorless plates 4 mm thick were obtained having the following characteristics:

Vicat temperature: >200° C.
Thermal stability of shape Martens*: 128° C.
ISO/R 75, A: 150° C.
Impact strength*: 7.1 cmkp/cm$^2$
*Measured on a standard size specimen.

Two more portions of the UP resin solution were stored at room temperature and at 35° C. Even after 2 months of storage, no alteration had occurred in either specimen. The UP resin was therefore stable in storage.

EXAMPLE 20

55.2 g (0.2 mole) of tetrachloro-m-xylyleneglycol, 11.4 g (0.115 mole) of maleic acid anhydride and 12.4 g (0.084 mole) of phthalic acid anhdyride were polycondensed, after the addition of 7.5 mg of hydroquinone, at a temperature slowly increasing to 220° C., until a molecular weight of 1980 (vapor pressure osmometer) was achieved. The UP resin contained 38% chlorine by weight. It was dissolved in styrene in a ratio of 55 weight-parts to 45 weight-parts of styrene, and hardened at 45° C. for 2 hours with 2 weight-percent of a 50% dibenzoylperoxide paste and 0.03 volume-% of dimethylaniline, and then cured for 4 hours at 135° C. The slightly cloudy casting, which contained 21% chlorine by weight, was resistant to combustion and had the following mechanical characteristics:

Vicat temperature: 190° C.
Thermal stability of shape Martens*: 113° C.
ISO/R 75, A: 125° C.
Impact strength*: 5.8 cmkp/cm$^2$
*Measured on a standard size specimen.

EXAMPLE 21

48.0 g (0.175 mole) of tetrachloro-m-xylyleneglycol, 1.55 g (0.025 mole) of ethyleneglycol, 11.4 g (0.115 mole) of maleic acid anhydride and 24.0 g (0.084 mole) of tetrachlorophthalic acid anhydride were polycondensed, after the addition of 7.5 mg of hydroquinone at a temperature slowly rising to 220° C. until a molecular weight of 1800 (vapor pressure osmometer) was attained. The UP resin contained 44% Cl by weight. It is dissolved in styrene in a ratio of 60 weight-parts in 40 weight-parts of styrene and hardened with 2 wt.-% of a 50% dibenzoylperoxide paste and 0.03 vol.-% of dimethylaniline at 40° C. for 2 hours, and cured at 135° C. for 4 hours. The casting, which contained 26% chlorine by weight, was resistant to combustion and had the following mechanical characteristics:

Vicat temperature: 196° C.
Thermal stability of shape Martens*: 108° C.
ISO/R 75, A: 121° C.
Impact strength*: 3.2 cmkp/cm$^2$
*Measured on a standard size specimen.

EXAMPLE 22

55.2 g (0.2 mole) of tetrachloro-m-xylyleneglycol, 9.28 g (0.08 mole) of fumaric acid, 22.88 g (0.08 mole) of tetrachlorophthalic acid anhydride and 6.32 g (0.04 mole) of phenylphosphonic acid were polycondensed, after the addition of 7.5 mg of hydroquinone, at a temperature slowly increasing to 220° C., until a molecular weight of 1800 (vapor pressure osmometer) was attained. The UP resin contained 45 wt.-% chlorine and 1.7 wt.-% of phosphorus. It was dissolved in styrene in a ratio of 59 weight parts to 41 weight parts of styrene, and hardened and cured as in Examples 20 and 21. The casting, which contains 26.5 wt.-% of chlorine and 0.8 wt.-% of phosphorus, is self-extinguishing and has the following mechanical characteristics:

Vicat temperature: 173° C.
Thermal stability of shape Martens*: 95° C.
ISO/R 75, A: 112° C.
Impact strength:* 4.7 cmkp/cm$^2$
*Measured on a standard size specimen.

What is claimed is:

1. A solution of an unsaturated polyester polymer soluble in styrene in an amount of 20 to 80% by weight and soluble in methylacrylate, methyl methacrylate, acrylonitrile, divinylbenzene and diallylphthalate and capable of being formed into a colorless transparent plate, said unsaturated polyester prepared by the condensation polymerization of a mixture of monomers, said mixture consisting essentially of:
   A. A member selected from the group consisting of fumaric acid, maleic acid, maleic acid anhydride, an alkali salt of maleic acid and an alkali salt of fumaric acid;
   B. A member selected from the group consisting of hexachlorenedomethylene tetrahydrophthalic acid, hexachlorophthalic acid, tetrahydrophthalic acid, adipic acid, their alkali salts or anhydrides, orthophthalic acid, its alkali salt, anhydride or lower alkyl ester, isophthalic acid, its alkali salt, anhydride or lower alkyl ester and terephthalic acid, its alkali salt, anhydride or lower alkyl ester;
   C. An alcohol selected from the group consisting of ethylene glycol, diethylene glycol, propanediol-1,2, butanediol-1,3, butanediol-1,4, neopentyl glycol and 1,4-bis-(hydroxymethyl)-cyclohexane; and
   D. 1 to 100 mol percent, relative to the sum of the C components, of a member selected from the group consisting of 2,3,5,6-tetrachloro-p-xylylene glycol, 2,3,4,6-tetrachloro-m-xylylene glycol, 2,3,5,6-tetrachloro-p-xylylene glycol-bis-(2,2-dimethyl-γ-hydroxyproyl ether), 2,3,5,6-tetrachloro-p-xylylene dichloride and 2,3,4,6-tetrachloro-m-xylylene dichloride, said solution containing a copolymerizable monomer, copolymerizable with said unsaturated polyester.

2. A solution according to claim 1 wherein said copolymerizable monomer is present in an amount between 20 and 80 percent by weight.

3. A polyester resin solution according to claim 2 wherein said copolymerizable monomer is styrene.

4. A polyester resin solution according to claim 1 containing between 40 and 70 percent by weight of said copolymerizable monomer.

UNITED STATES PATENT AND TRADEMARK OFFICE
CERTIFICATE OF CORRECTION

PATENT NO. : 4,134,934
DATED : January 16, 1979
INVENTOR(S) : Georg Blumenfeld et al It is certified that error appears in the above-identified patent and that said Letters Patent are hereby corrected as shown below:

Column 11, line 71 (which is not completely printed) should read as follows:
-- and 200°C until a molecular weight of 1800 (vapor --.

Column 15, line 36, delete "b" before "1570".

Column 15, line 40, "moled" should read -- mold --.

Column 15, line 47, "5.8 L cmkp/cm$^2$" should read -- 5.8 cmkp/cm$^2$ --

*Signed and Sealed this*

*Twenty-second* Day of *May 1979*

[SEAL]

Attest:

RUTH C. MASON
*Attesting Officer*

DONALD W. BANNER
*Commissioner of Patents and Trademarks*